United States Patent [19]

Pietrafitta et al.

[11] Patent Number: 5,355,897
[45] Date of Patent: Oct. 18, 1994

[54] METHOD OF PERFORMING A PYLOROPLASTY/PYLORECTOMY USING A STAPLER HAVING A SHIELD

[75] Inventors: Joseph J. Pietrafitta, Minnetonka, Minn.; Ronald D. Adams, Cincinnati, Ohio

[73] Assignee: Ethicon, Inc., Somerville, N.J.

[21] Appl. No.: 869,981

[22] Filed: Apr. 16, 1992

[51] Int. Cl.⁵ .............................................. A61B 17/00
[52] U.S. Cl. .................................... 128/898; 606/1; 227/179; 227/180; 227/181
[58] Field of Search ............. 606/142, 143, 151, 153, 606/1; 227/175, 176, 178-181, 19, 901

[56] References Cited

U.S. PATENT DOCUMENTS

| | | | |
|---|---|---|---|
| 4,328,805 | 5/1982 | Akopov et al. | 606/139 |
| 4,700,703 | 10/1987 | Resnick et al. | 227/180 |
| 4,817,847 | 4/1989 | Redtenbacher et al. | 227/19 |
| 5,197,648 | 3/1993 | Gingold | 227/179 |

FOREIGN PATENT DOCUMENTS 3300768  4/1985  Fed. Rep. of Germany ...... 227/179

OTHER PUBLICATIONS

"Experimental Transperitoneal Laproscopic Pyloroplasty", Joseph J. Pietrafitta, MD., et al., Surgical Laparoscopy and Endoscopy, vol. 2, No. 2, pp. 140–110, (1992).

Primary Examiner—Stephen C. Pellegrino
Assistant Examiner—Jeffrey A. Schmidt

[57] ABSTRACT

A pyloroplasty/pylorectomy shield having a base member and a proximally extending shield member. The pyloroplasty/pylorectomy shield has attachment means for engagement with a circular stapler. The pyloroplasty/pylorectomy shield also has dilation means for progressively dilating a sphincter. The pyloroplasty/pylorectomy shield is used with a circular stapler to perform a pyloroplasty/pylorectomy. Also disclosed is a method of performing a pyloroplasty/pylorectomy using the pyloroplasty/pylorectomy shield of the present invention. The pyloroplasty/pylorectomy shield has numerous advantages including reduced trauma, decreased misalignment resulting in improved stapling and improved positioning of the pyloroplasty/pylorectomy.

1 Claim, 6 Drawing Sheets

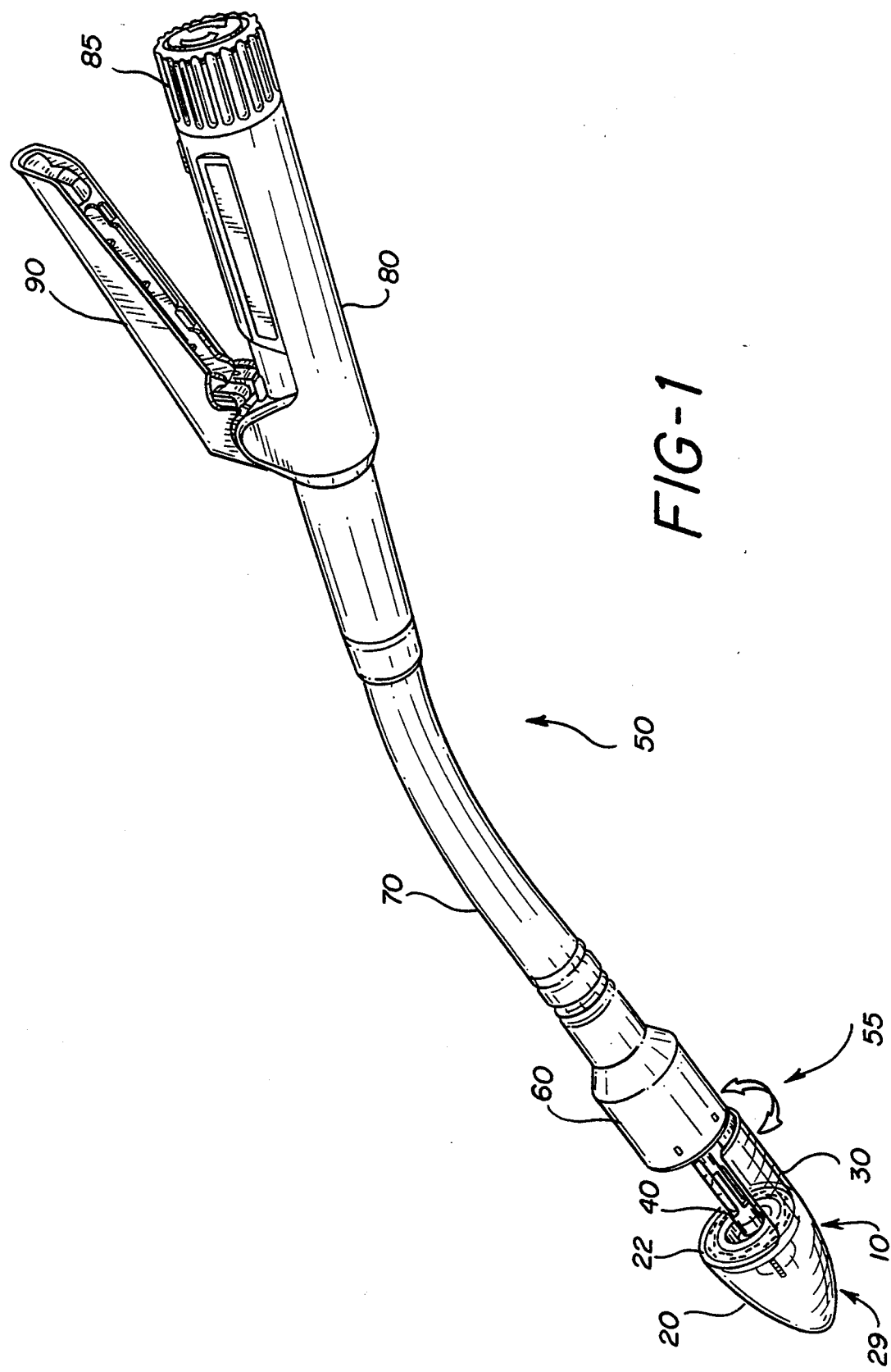

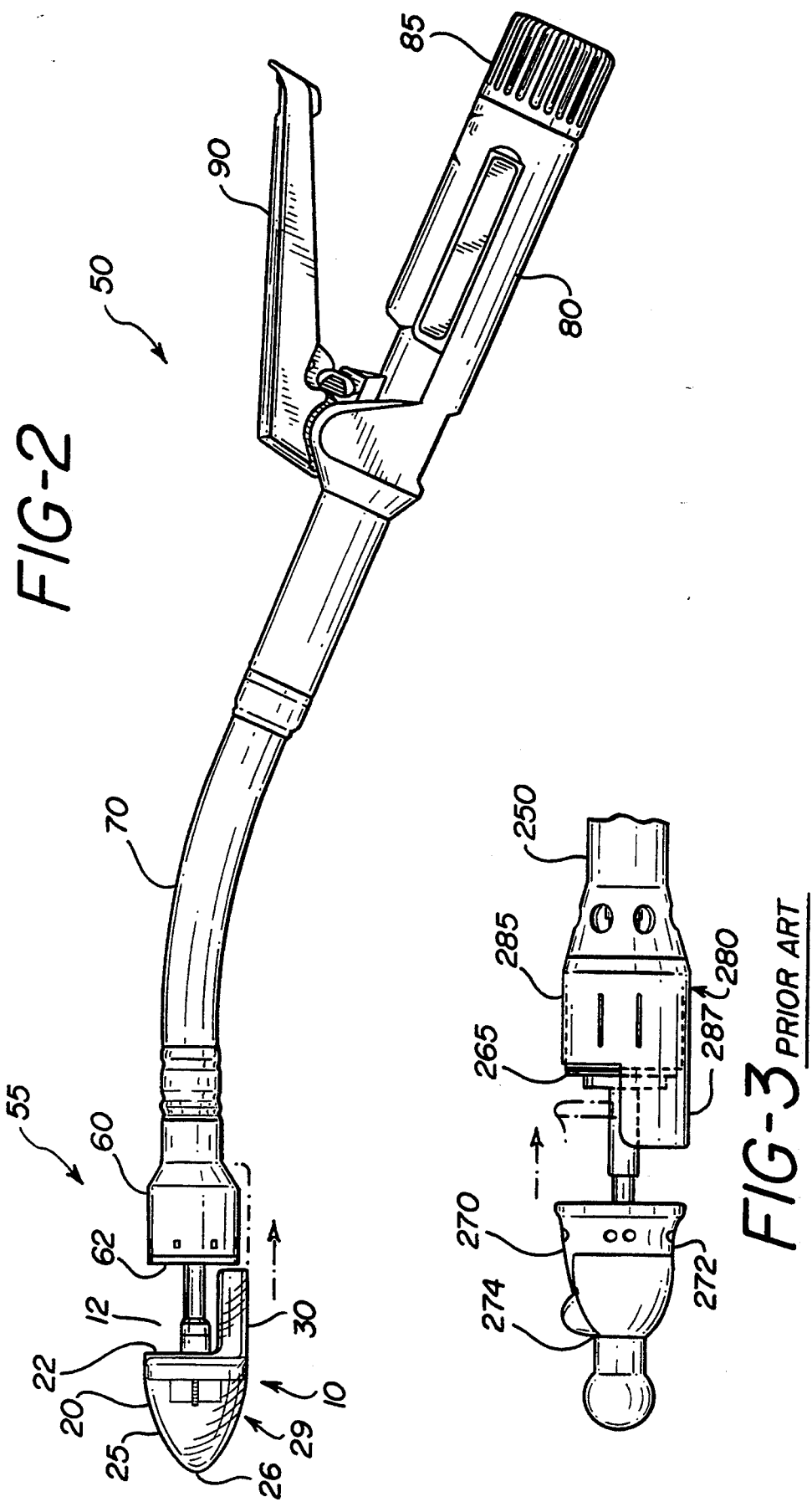

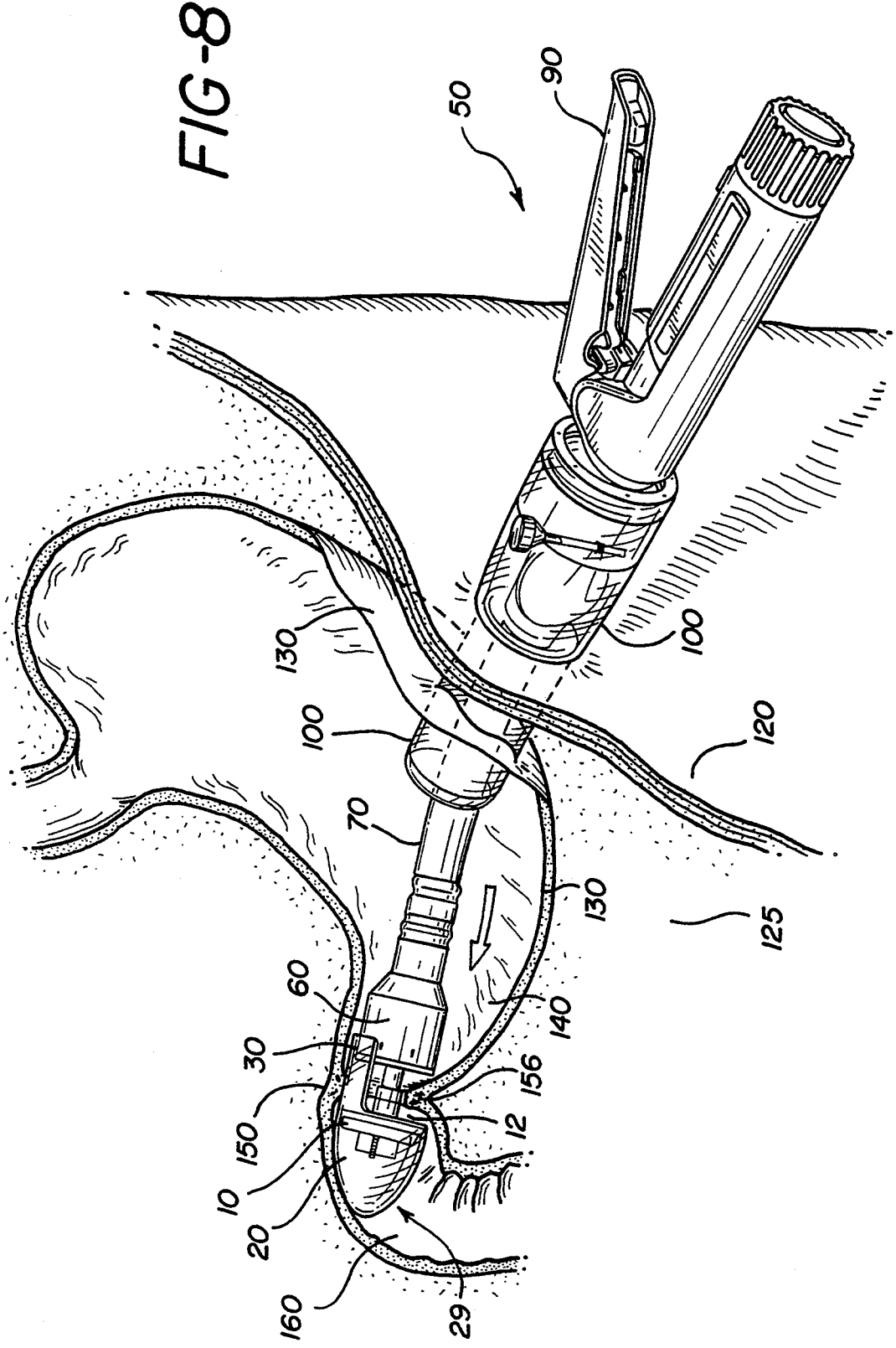

METHOD OF PERFORMING A PYLOROPLASTY/PYLORECTOMY USING A STAPLER HAVING A SHIELD

TECHNICAL FIELD

The field of art to which this invention relates is a surgical instrumentation, in particular, endoscopic surgical instruments.

Background of the Invention

Endoscopic surgical techniques have gained wide acceptance among surgeons and the patient population. There are many benefits associated with the use of endoscopic surgical techniques when compared to conventional, open surgical techniques. The benefits include reduced avenues for infection, reduced trauma to the patient, reduced hospital stay and a decrease in postoperative recuperation time, and decreased scarring. Accordingly, endoscopic surgical instruments have been developed for use in these endoscopic surgical procedures. Endoscopic as used herein is defined to include endoscopic, arthroscopic, laparoscopic and thoracoscopic.

Conventionally, in order to treat certain conditions involving ulcers of the stomach and duodenum, it has been necessary to perform an operation known as truncal vagotomy. It is believed that such ulcers are attributable to excess secretion of acid by the stomach. This excess stomach acid (over and above the quantity needed for normal digestion of food) attacks the lining of the stomach and the lining of the upper duodenum. In order to remediate this condition, the vagus innervation of the stomach is interrupted by the performance of the truncal vagotomy. When performing a truncal vagotomy it is also necessary to perform a drainage procedure. A pyloroplasty is one type of drainage procedure. The pyloroplasty ensures drainage of the gastric antrum following vagotomy and therefore partially eliminates the antral phase of gastric secretion. A pyloroplasty is a surgical procedure which involves the reshaping of the pylorus and the subsequent attachment of the lower part of the stomach proximal to the pylorus to the anterior portion of the duodenum distal to the pylorus. The attachment, i.e., closure, is made adjacent to either side of the reshaped pylorus. In the past, this operation has been performed using conventional, open surgical techniques, for example, the Heineke-Mikulicz pyloroplasty or the Finney pyloroplasty. In these techniques, the pyloric sphincter muscle is cut with conventional scalpels and then the stomach is sutured to the duodenum or the stomach and duodenum are closed in the direction opposite to which it is opened. More recently, circular staplers have been developed to perform a pyloroplasty/pylorectomy. The circular staplers simultaneously cut out a section of the pylorus while stapling the stomach to the duodenum.

It has now been found to be advantageous to perform a pyloroplasty/pylorectomy using endosurgical techniques. When performing an endoscopic pyloroplasty/pylorectomy, typically, a large diameter trocar is inserted through the abdominal wall and through the wall of the stomach into the interior of the stomach. Then, a conventional circular stapler particularly adapted to performing a pyloroplasty/pylorectomy is inserted through the trocar and to the site of the pylorus. The anvil and the staple cartridge head of the stapler are then maneuvered into the pylorus and positioned such that a section of the pylorus is removed as the distal part of the stomach is stapled to the proximal duodenum. Due to the nature of a circular stapler, or, as it is also known, an intraluminal stapler, it is necessary to shield off a portion of the opening or gap between the anvil of the stapler and the stapler cartridge when performing a pyloroplasty/pylorectomy so that the posterior wall of the pylorus will not be cut or stapled. When performing an anastomosis on tubular organs, the circular stapler is designed to cut a circular piece of the organ by making 360 degree incision. However, when performing a pyloroplasty/pylorectomy, it is neither desirable nor necessary to make a 360 degree cut which would remove the entire pylorus, rather it is desired to only remove a portion of the pyloric ring along a circular arc, e.g., about 90 degrees to 240 degrees. In order to accomplish this type of partial cut, it is necessary, as previously mentioned, to shield off a portion of the gap between the anvil and the staple cartridge.

A conventional circular stapler is designed to capture tissue in the gap between the distal anvil and the proximal staple cartridge, and to then engage the tissue and simultaneously cut and staple the tissue in the gap when actuated. In order to adapt the circular stapler for use in pyloroplasty/pylorectomy, a conventional pyloroplasty/pylorectomy shield was developed which is typically mounted to the circular stapler. The conventional pyloroplasty/pylorectomy shield consists of a proximal tubular member adapted to fit about the staple cartridge and a shield member extending distally from the tubular member and covering in part the gap between the anvil and the staple cartridge. In order to use a circular stapler which has been adapted for performing a pyloroplasty/pylorectomy, the anvil and staple cartridge, having a conventional pyloroplasty/pylorectomy shield mounted thereto, are positioned within a patient's pylorus. The section of the pylorus which is to be excised falls into the gap between the anvil and the staple cartridge. However, the shield prevents an arcuate posterior section of the pylorus from falling into the gap between the anvil and the staple cartridge, thereby preventing that portion from being cut and stapled by the circular stapler.

There are several deficiencies associated with a conventional pyloroplasty/pylorectomy shield. The conventional pyloroplasty/pylorectomy shield has a proximal tubular end which is loosely mounted to the staple cartridge. Since the proximal tubular end of a conventional pyloroplasty/pylorectomy shield is not rigidly attached to the staple cartridge, it is possible for the pyloroplasty/pylorectomy shield to pivot out of alignment or to rotate about the staple cartridge during insertion and positioning within the pylorus. This may result in staple misfiring with either no staple formation or poor staple formation. Or, it may result in misalignment and poor positioning of the pyloroplasty/pylorectomy.

Another disadvantage associated with a conventional pyloroplasty/pylorectomy shield is that the proximal tubular member is mounted to the cartridge of the stapler and the shield member extends axially and distally therefrom. Consequently, as the distal end of the stapler having the mounted pyloroplasty/pylorectomy shield is inserted into the stomach or through the pylorus, it is possible for the distal shield member of the pyloroplasty/pylorectomy shield to possibly pierce or damage the stomach wall, the pylorus, or the duodenum.

Another deficiency associated with a conventional pyloroplasty/pylorectomy shield used with a conventional circular stapler is that the contour of a conventional anvil head does not provide for progressive dilation of the pylorus. Conventional anvil heads have blunt distal surfaces or irregularly shaped distal surfaces or combinations thereof. Since the anvil contours are blunt and/or irregular, when the surgeon inserts the anvil through the pylorus the resulting dilation of the pylorus is sudden, possibly resulting in tears or damage to the pylorus.

Another deficiency associated with conventional pyloroplasty/pylorectomy shields relates to the length of the distally extending shield member. If the axial length of the shield member is too short, the back wall of the stomach or duodenum can become entrapped between the proximal face of the anvil and the distal edge of the shield member as the surgeon adjusts the gap between the anvil and the stapler cartridge in order to properly engage the tissue prior to performing the pyloroplasty/pylorectomy. This may result in injury to or perforation of the pylorus, stomach or duodenum. Conversely, if the shield member length is too long, then it may protrude a significant distance beyond the distal end of the anvil and can by its blunt, rough nature injure the back wall of the bowel as it is being introduced.

Yet another deficiency associated with the conventional pyloroplasty/pylorectomy shields used with conventional circular staplers is that, typically, a relatively large diameter stapler must be used to perform the anastomosis thereby aggravating the traumatic effects of pyloric dilation.

What is needed in this art is a pyloroplasty/pylorectomy shield which overcomes these deficiencies.

SUMMARY OF THE INVENTION

A pyloroplasty/pylorectomy shield is disclosed. The pyloroplasty/pylorectomy shield can be used with a circular stapler to perform a pyloroplasty/pylorectomy on a pylorus. The pyloroplasty/pylorectomy shield comprises a base member having an anvil means mounted to a first, proximal end of the base member. Attachment means are mounted to the first proximal end of the base member for engagement with the circular stapler. The base member has dilation means extending distally from the other end of the member for progressively dilating a sphincter. A pyloroplasty/pylorectomy shield member extends axially and proximally from the first end of the member.

Another aspect of the present invention is the combination of a pyloroplasty/pylorectomy shield and a circular stapler. The pyloroplasty/pylorectomy shield comprises a base member having anvil means mounted to a first, proximal end of a base member. Attachment means are mounted to the first end of said base member for engagement with the circular stapler. A pyloroplasty/pylorectomy shield member extends axially and proximally from the first end of said base member. And, dilation means extend distally from the other, distal end of the base member for dilating a sphincter.

Yet another aspect of the present invention is a method of using the above-described pyloroplasty/pylorectomy shield and combination to perform a pyloroplasty/pylorectomy, either endoscopically or using conventional, open surgical techniques.

The foregoing and other features and other advantages of the present invention will become more apparent from the following description and accompanying drawings.

BRIEF DESCRIPTION OF THE DRAWINGS

FIG. 1 is a perspective of the view of the pyloroplasty/pylorectomy shield of the present invention attached to a circular stapler.

FIG. 2 is a side view of the pyloroplasty/pylorectomy shield of the present invention mounted to a circular stapler.

FIG. 3 is a side view of a pyloroplasty/pylorectomy shield of the prior art mounted to the cartridge of a circular stapler having an embodiment of a conventional anvil.

FIG. 8 is a perspective of the view of the pyloroplasty/pylorectomy shield of the present invention inserted through a trocar into the stomach of a mammal and positioned in the pylorus prior to performing a pyloroplasty/pylorectomy.

BEST MODE FOR CARRYING OUT THE INVENTION

Figure 4:
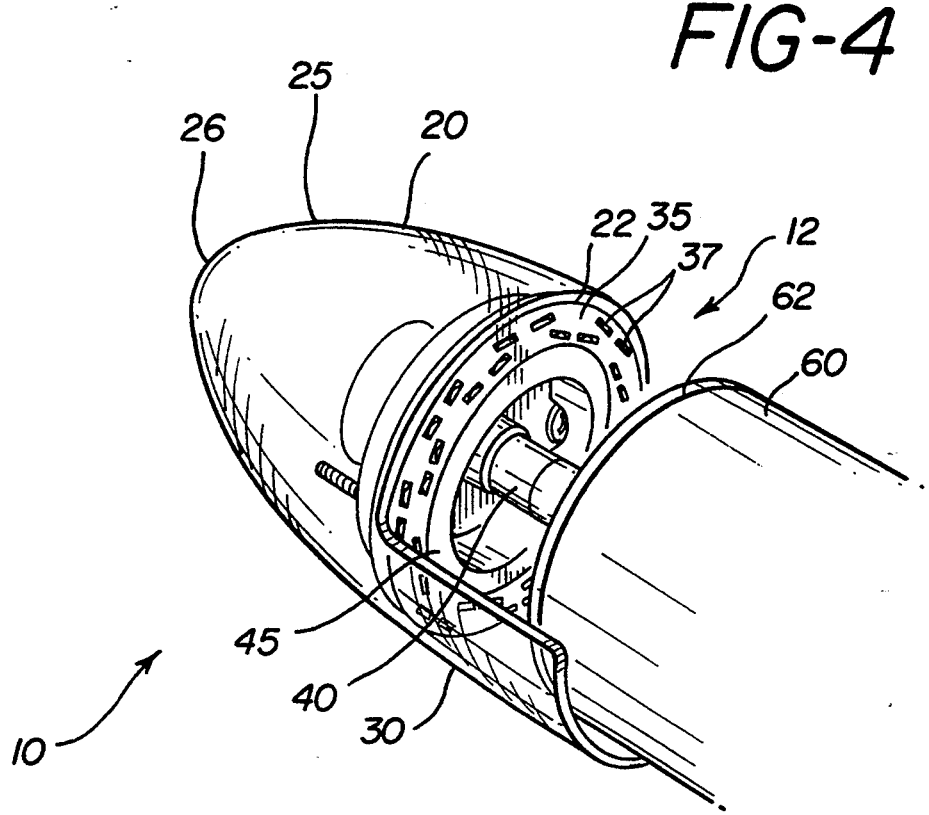
FIG. 4 is a partial perspective view of the pyloroplasty/pylorectomy shield of the present invention mounted to a circular stapler.
Figure 7:
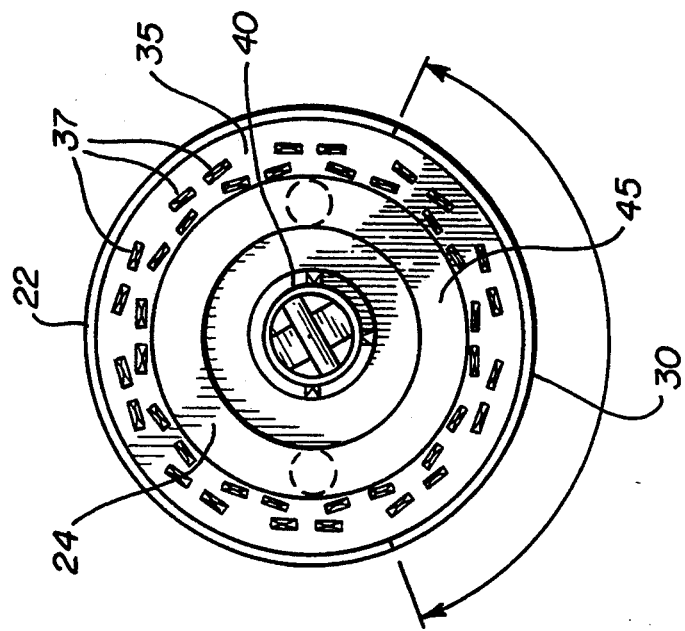
FIG. 7 is a view of the proximal end of the pyloroplasty/pylorectomy shield of FIG. 6.
Figure 6:
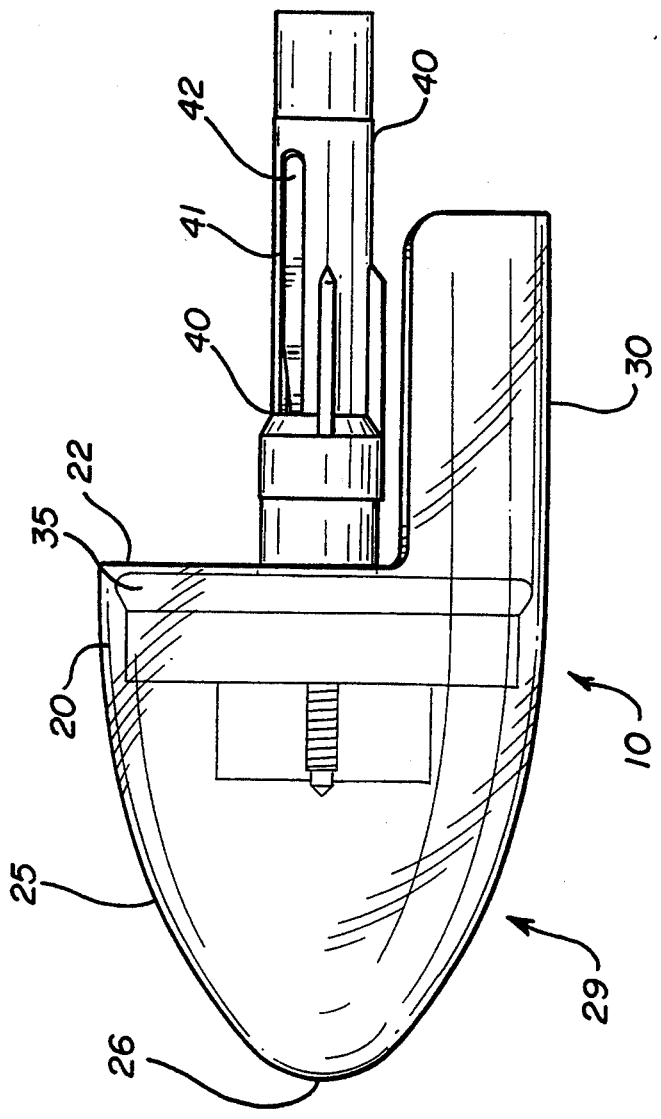
FIG. 6 is a side view of the pyloroplasty/pylorectomy shield of the present invention.

The pyloroplasty/pylorectomy shield 10 of the present invention connected to a conventional intraluminal (i.e., circular) stapler 50 is seen in FIGS. 1, 2 and 4. The pyloroplasty/pylorectomy shield 10 is also illustrated in FIGS. 6 and 7. The pyloroplasty/pylorectomy shield 10 is seen to have an ellipsoid base member 20 having proximal end 22 and distal end 25. Circular conventional anvil ring 35, having forming cavities 37, is peripherally mounted to the proximal end 22 of member 20. Resilient ring 45 and shaft 40 are mounted in cavity 24 contained in the proximal end 22 of member 20. Resilient ring 45 is a conventional ring comprising a pliable material for engaging circular cutting blade 68 (not shown) of stapler 50. Shaft 40 is a conventional anvil mounting shaft having a longitudinal slot 41 containing longitudinal spring members 42. The spring members 42 engage a mounting member (not shown) extending from the distal end of the stapler 50. Shaft 40 is a mounting means for engagement or attachment of the shield 10 to a circular stapler. As illustrated, the mounting means is such that the shaft 40 may be disengaged form the stapler 50. In a preferred embodiment, the shaft 40 is not disengageable from the stapler 50 although still capable of being displaced axially with respect to the stapler 50. The distal end 25 of pyloroplasty/pylorectomy shield 10 is seen to taper in a curved manner to a tip 26 to form, along with the base member 20, a dilating means 29 in order to provide the pyloroplasty/pylorectomy shield 10 with dilating capability. The shield 10 may have a variety of dilating means 29 extending distally from base member 20. It is particularly preferred that the dilating means 29 have an ellipsoidal shape as seen in FIG. 6. Other shapes may include a substantially conical shape having a blunt tip which can serve as a probe, or, any shape effective to progressively and gradually dilate a sphincter without traumatizing the sphincter. If desired, the dilating means may have external screw threads to assist in dilation.

Extending proximally in an axial manner from the proximal end 22 of the member 20 is the pyloroplasty/pylorectomy shield member 30. The shield member 30 is an arcuate member having, preferably, the same outer radius as the outer radius of the member 20 and an inner radius greater than the outer radius of the staple cartridge 60 so that the shield can pass over the outside of the stapler cartridge 60. If one were willing to accept the disadvantages which may be attendant, if any, the shield member 30 could have a greater or lesser outside radius than the radius of base member 20. Of course, this may require corresponding changes to the design and shape of staple cartridge 60.

Referring to FIG. 1 and FIG. 2, the surgical stapler 50 is seen to be a conventional surgical stapler having a cartridge 60, a tubular frame 70, and a handle 80. The handle 80 has actuating lever 90 for actuating cartridge 60 and rotatable knob 85 for displacing shield 10 axially, both distally and proximally, with respect to the cartridge 60. Conventional circular stapling instruments are disclosed in U.S. patent application Ser. No. 749,393 filed on Aug. 23, 1991 which is incorporated by reference.

The cartridge 60 contains a plurality of staples displaced circumferentially in cavities for engagement with the anvil ring 35, and, a circular cutting blade 68 for engagement with resilient ring 45. The staples and cutting blade 68 are actuated through conventional actuating means by the handle 90. Proximal knob 85 rotatably engages conventional means for displacing shield 10 axially with respect to cartridge 60, thereby controlling the gap 12 between shield 10 and cartridge 60. It will be appreciated that although the shield member 30 is shown in a particular location with respect to stapler 50 and cartridge 60 in FIG. 1 and FIG. 3, the shield member 30 may be positioned in any desired position, such as illustrated in FIG. 8, by rotating the pyloroplasty/pylorectomy shield 10 with respect to the cartridge 60.

Figure 9:
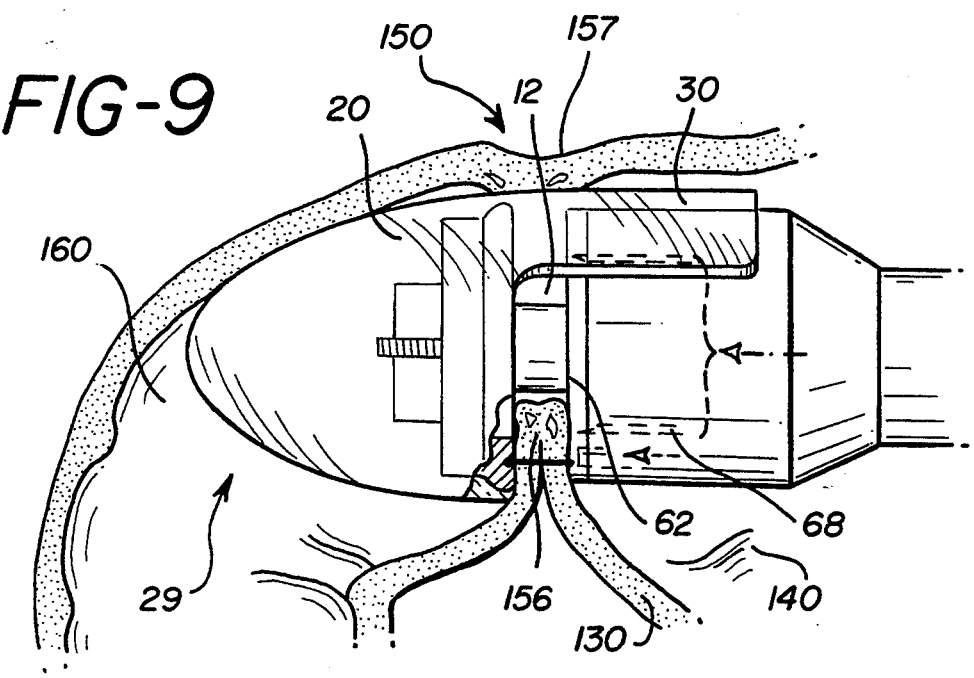
FIG. 9 is a side view of the pyloroplasty/pylorectomy shield of the present invention and a staple cartridge within the pylorus wherein the anterior section of the pylorus is in the gap between the shield and the cartridge and further wherein the shield member is preventing the posterior portion of the pylorus from entering the gap.

Referring to FIG. 8 and FIG. 9, when inserting the distal end of the stapler 50 containing the pyloroplasty/pylorectomy shield 10 and the staple cartridge 60 through the pylorus 150, the pyloroplasty/pylorectomy shield 10 will be displaced distally with respect to the cartridge 60 by rotating knob 85 so that there is a sufficient gap 12 for a section of the pylorus 150 to fall into. The thickness of the gap 12 will depend upon the thicknesses of the stomach wall, duodenum wall and pylorus. The amount of pylorus 150 which will fall into the gap 12 is dependent upon the size of pyloroplasty/pylorectomy shield member 30, specifically with regard to the number of degrees of arc of the shield member 30. The degrees of arc will be sufficient to effectively shield out the posterior pylorus to allow an effective pyloroplasty/pylorectomy to be performed. It will be appreciated by those skilled in the art that the length of the pyloroplasty/pylorectomy and thus the effectiveness of the drainage procedure can be regulated by the length (i.e., arc) of the gap. Typically, the degrees of arc of shield member 30 will be about 60° to about 180°, more typically to about 90° to about 160°, preferably about 110° to about 130° and even more preferably about 120°. It will be appreciated that the number of degrees of gap 12 arc are equal to the number of degrees of arc of shield member 30 subtracted from 360. The shield member 30 will be sufficiently long to effectively cover the gap 12 required to perform a pyloroplasty/pylorectomy. The shield member 30 will typically have a length of about 5 mm to about 40 mm, preferably about 10 mm to about 20 mm. The diameter of the base member 20 will be sufficient to provide a base for effectively mounting the anvil 35 and the dilation means. The maximum diameter of the base member 20 will typically be about 10 mm to about 50 mm, more typically about 20 mm to about 40 mm, and preferably about 20 mm to about 30 mm, although any effective diameter size may be used.

Figure 10:
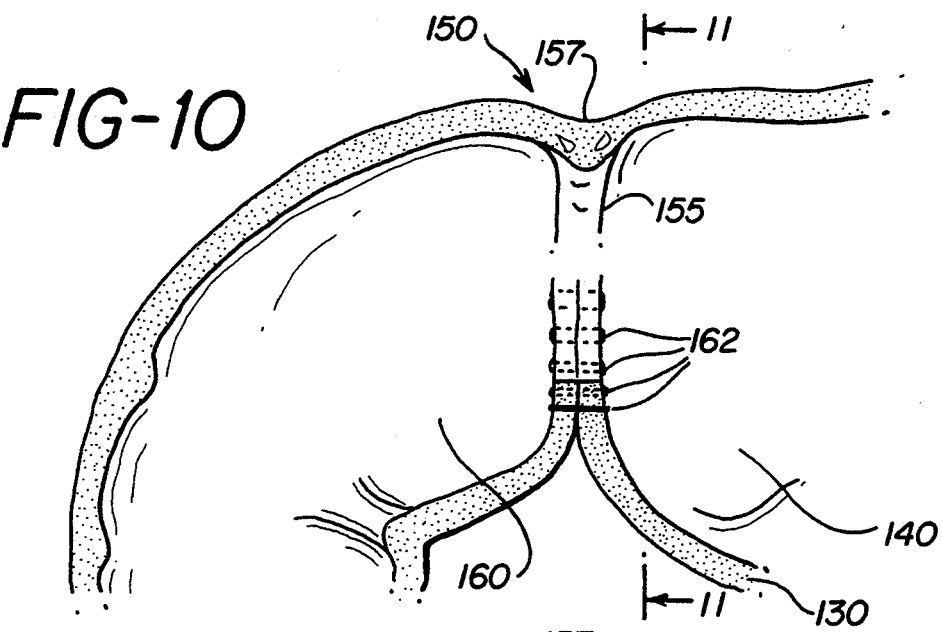
FIG. 10 is a view of a side section through the lower stomach, upper duodenum and pylorus illustrating the completed pyloroplasty/pylorectomy.
Figure 11:
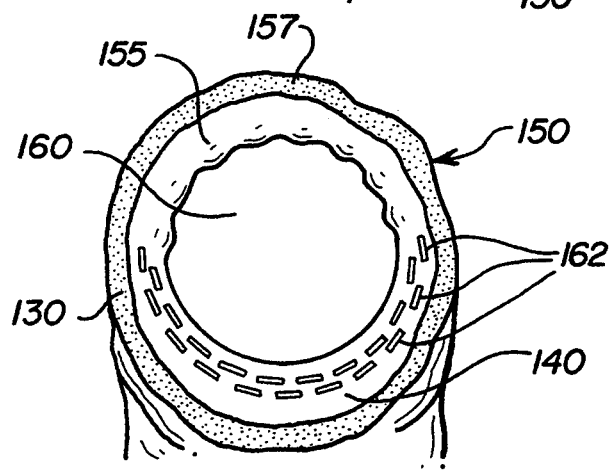
FIG. 11 is a sectional view through the lower stomach showing an end view of the pyloroplasty/pylorectomy of FIG. 10.

Endoscopic surgical techniques are widely known, e.g., such techniques are disclosed in the following publications which are incorporated by reference, Laporascopy For Surgeons, B. A. Salky, M.D., Igaku-Shoin, New York (1990), and Textbook Of Laparoscopy, J. F. Hulka, M.D., Grune & Straton (1985). Conventional endoscopic techniques would typically be employed in the performance of an endoscopic pyloroplasty/pylorectomy. An endoscopic surgical procedure utilizing the pyloroplasty/pylorectomy shield 10 of the present invention to perform a pyloroplasty/pylorectomy is performed in the following manner. Initially, a the patient is anesthetized using conventional anesthesia and anesthesiology techniques effective to produce an anesthetized state. Typically, the patient is then insufflated with a sterile gas such as carbon dioxide in order to inflate the body cavity to give the surgeon room to maneuver the instruments. When performing an endoscopic pyloroplasty/pylorectomy, the abdominal cavity of the patient will typically be insufflated sufficiently to induce an effective pneumoperitoneum. Then, conventional trocars having piercing tip obturators and trocar cannulas are inserted through abdominal wall 120 and into the abdominal cavity 125. The trocar obturators are then removed leaving trocar cannulas for insertion of various endoscopic surgical instruments including endoscopes, sutures, manipulating tools, and the like. When performing the pyloroplasty/pylorectomy, initially a conventional 10 mm trocar cannula is inserted through the abdominal wall 120 and through the stomach wall 130 into the interior of stomach 140. Since the circular stapler 50 used to perform the pyloroplasty/pylorectomy will typically have a distal head 55 having a diameter greater than 10 mm, it is then necessary to replace the 10 mm trocar cannula with a larger conventional trocar cannula 100, such as a 33 mm trocar cannula, using conventional techniques. Referring to FIG. 8 and FIG. 9, when the larger diameter trocar cannula 100 is in place, the conventional circular stapler 50 having the pyloroplasty/pylorectomy shield 10 of the present invention mounted thereto is inserted through the trocar 100 and into the stomach 140. The dilating means 29 of the pyloroplasty/pylorectomy shield 10 is then maneuvered to and inserted into the pylorus 150. Then, the pylorus 150 is progressively dilated until the pylorus is positioned in the gap 12 between the proximal end 22 of the pyloroplasty/pylorectomy shield 10 and the distal end 62 of the cartridge 60. The base member 20 is now positioned within the duodenum 160 while the cartridge 60 is positioned in the stomach 140. The surgeon then positions the pyloroplasty/pylorectomy shield member 30 of the pyloroplasty/pylorectomy shield 10 by rotating the stapler 50 within the trocar cannula such that the section of the pylorus 150 which the surgeon desires to excise falls within the unshielded gap 12 and is engaged between the proximal end 22 of the pyloroplasty/pylorectomy member 10 and the distal end 62 of the cartridge 60. The surgeon adjusts the thickness of the gap 12 such that it is sufficient to provide effective stapling. This is done by rotating adjusting knob 85 which causes shield 10 to translate axially in a proximal direction. It is preferred that a conventional invaginator be used to assure that the section 156 of the pylorus 150 which is to be excised remains within the gap 12 as the gap 12 is adjusted. The conventional invaginator is typically inserted through a 10 mm trocar and is used to apply a radial force (inward) upon the pylorus. Then, the surgeon actuates the stapler 50 by squeezing the actuating lever 90 causing the staples to be driven through the tissue in the gap 12 while simultaneously causing the cutting blade 68 to cut a section 156 of the pylorus 150 contained within gap 12. As can be seen in FIG. 10 and FIG. 11, this results in rows of formed staples 162 connecting the section of the lower end of the stomach 140 with the upper end of the duodenum 160 where the section 156 of pylorus 150 has been cut out. The stapler 50 and the pyloroplasty/pylorectomy shield 10 are then removed from the pylorus 150 and stomach 140 along with the excised section 156 of pyloris 150 through the trocar cannula 100.

Figure 5:
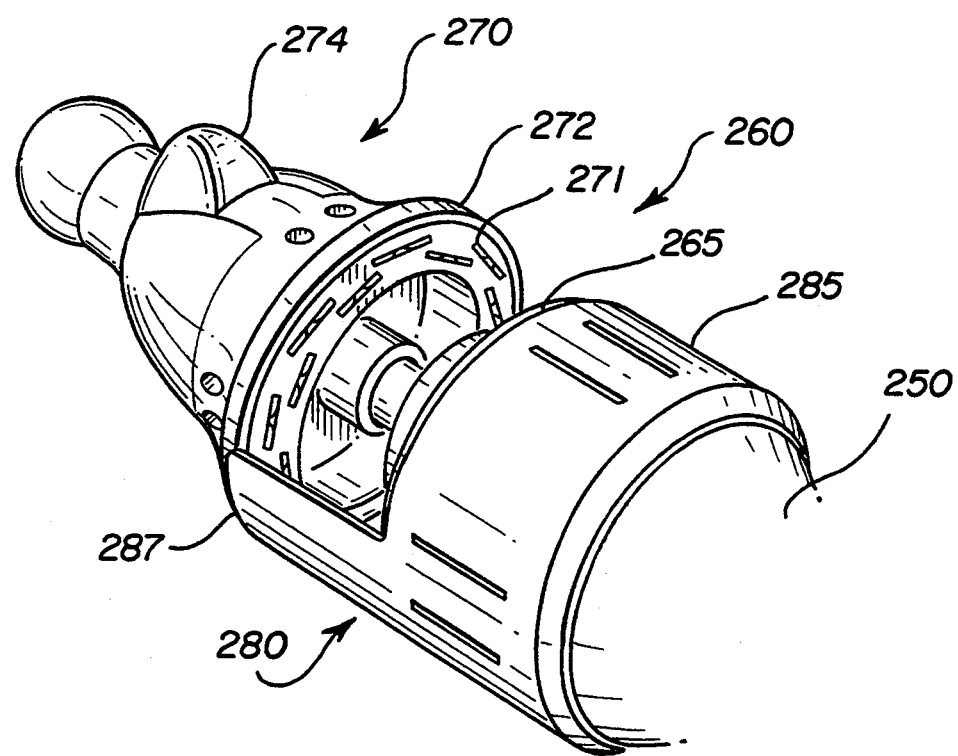
FIG. 5 is a partial perspective of a conventional pyloroplasty/pylorectomy shield mounted to the cartridge of a conventional circular stapler having an embodiment of a conventional anvil.

Referring to FIG. 3 and FIG. 5, the distal end 160 of circular stapler 250 of the prior art having a conventional pyloroplasty/pylorectomy shield 280 is seen. The pyloroplasty/pylorectomy shield 280 is seen to consist of a tubular ring-like member 285 which fits over the staple cartridge 265 and which can be rotated with respect to the cartridge 265. An arcuate shield member 287 extends distally from the tubular member 285. A rod 267 for engaging the cartridge 265 extends proximally from the proximal end of the conventional anvil member 270, and, an anvil 271 is peripherally mounted to said proximal end. The anvil member 270 is seen to have an outwardly extending flange portion 272 and a relatively blunt and irregularly shaped distal end 274. It can be appreciated that the anvil member 270 is not conducive to dilating a sphincter such as the pylorus. It can also be appreciated that there are several deficiencies associated with the pyloroplasty/pylorectomy shield 280 of the prior art. It can be appreciated by those skilled in the art that since the shield 280 is free to rotate about the cartridge 265, it is possible that the shield 280 may rotate inadvertently during insertion such that the surgeon engages a section of the pylorus which was not intended thereby resulting in a piece of the pylorus being cut out which should have remained intact. Another major deficiency of the pyloroplasty/pylorectomy shield 280 is that because it is configured to extend distally from the cartridge 265 of the stapler 250, it is possible for the shield member 287 to pierce or tear the stomach lining, the pylorus or the duodenum during insertion. Yet another deficiency is that since the shield 280 is mounted relatively loosely to cartridge 265 so that it is free to rotate about the cartridge 265, the shield 280 may pivot about the longitudinal axis of the cartridge 265 during insertion, thereby causing misalignment of the anvil member 270 with respect to the staple cartridge 265. Such misalignment may result in misfiring of the staples. Such misalignment may also result in misalignment or poor positioning of the pyloroplasty/pylorectomy. Yet another disadvantage is that the shield 280 may cause a piece of the pylorus to become displaced between the anvil member 270 and the shield member 287 thereby tearing or cutting a portion of the pyloric tissue which was unintended, or causing misalignment of the anvil member 270 with respect to the staple cartridge 265. Another disadvantage of the prior art configuration is that the anvil member 270 does not have a dilating means. This can result in the pylorus being torn or ripped as the surgeon attempts to insert the blunt and irregularly shaped distal end 272 of the anvil member 270 into the pylorus. The pyloroplasty/pylorectomy shield 10 of the present invention, surprisingly and unexpectedly, overcomes these disadvantages. The progressively tapered, gradual dilating means 29 of the member 20 is easily inserted into the constricted pylorus sphincter 150, and readily and progressively dilates the sphincter 150 without traumatizing and/or tearing the sphincter muscle and tissue surrounding the sphincter 150. Furthermore, as can be seen in FIG. 9, since the shield 30 extends from the proximal end 22 of the member 20, it can be appreciated that during insertion through the pylorus 150 the risk of the shield member 30 damaging or tearing the pylorus 150 or damaging or puncturing the stomach 140 or duodenum 160 is substantially eliminated. Furthermore, since the shield member 30 is integral with the member 20 and is not free to rotate about the member 20, the surgeon will be more easily be able to position the section of the pylorus which he intends to excise in the gap 12 between the proximal end 22 of the member 20 and the distal end 62 of the stapling cartridge 60. In addition, since the shield member 30 is affixed to the member 20, it is less likely to cause the anvil 37 to displace and become misaligned with respect to the cartridge 60, thereby reducing or preventing the misfiring of the staples into the anvil. Yet another advantage of the shield 10 is that it eliminates the need for an additional piece to perform a pyloroplasty/pylorectomy. That is, a conventional pyloroplasty/pylorectomy configuration requires a separate anvil member 280, a separate cartridge 200 and a separate pyloroplasty/pylorectomy shield 280 mounted to a conventional stapler 250. However, the pyloroplasty/pylorectomy configuration of the present invention requires only the cartridge 60 and the shield 10 since the anvil 35 is integral with the shield 10.

Still yet another advantage of the pyloroplasty/pylorectomy shield 10 is that the axial length of the shield member 30 is less critical than that of a conventional pyloroplasty/pylorectomy shield since the shield member 30 extends axially in proximal direction eliminating deficiencies associated with overly short or long conventional shield members.

The shield 10 can be made out of conventional materials used to manufacture surgical instruments, including plastics, metals and combinations thereof. It can be appreciated that it is particularly preferred to mold the member 20 together with the shield member 30 in a single unitary piece to produce the shield 10 from conventional, medical-grade plastic materials such as polycarbonate, polypropylene, and ABS, using conventional injection molding techniques. It is particularly preferred to use polycarbonate plastic material. It is also possible to manufacture base member 20 and shield member 30 separately and then attach the members using conventional attachment methods. The shield 10 may be made from transparent or opaque materials.

It will be appreciated by those skilled in the art that the pyloroplasty/pylorectomy shield 10 of the present invention can be used in conventional open pyloroplasty procedures as well as endoscopic pyloroplasty/pylorectomy procedures. The advantages of the pyloroplasty/pylorectomy shield 10 would be similar in an open procedure. In a conventional open pyloroplasty procedure, the surgical technique and method would be almost identical to the endoscopic method and procedure except that, for example, trocars would not be used to access the pylorus. It should also be noted that in an open procedure, in contrast to an endoscopic procedure, typically no portion of the pyloric muscle is excised.

The following example is illustrative of the principals and practice of the present invention, although not limited thereto.

EXAMPLE

A mammal is anesthetized using a sufficient dose of conventional anesthesia and employing conventional anesthesiology techniques effective to induce an anesthetized state. An endotracheal tube is inserted and the patient is ventilated as required. Next, the abdominal cavity of the mammal is insufflated using conventional techniques with a sufficient amount of a sterile conventional gas. Then, several conventional 10 mm trocars are inserted through the abdominal wall 120 into the abdominal cavity 125 of the mammal. The trocar obturators are removed from the trocars leaving the trocar cannulas in place. At least one trocar is inserted through the stomach wall 130 and into the stomach 140 of the mammal. Then, using conventional techniques, the 10 mm trocar cannula in the stomach is replaced with a conventional 33 mm trocar cannula 100. A conventional trocar is also inserted through the abdominal wall 120 through the stomach wall 130 and into the stomach 140. The trocar obturator is removed and an endoscope is inserted through the conventional 10 mm trocar cannula into the stomach. Then, the surgeon inserts a circular stapler 50 having a pyloroplasty/pylorectomy shield 10 of the present invention slidably mounted to the distal end 55 of stapler 50. The surgeon maneuvers the pyloroplasty/pylorectomy shield 10 and the stapler 50 up to the pylorus 150. The surgeon then pushes the proximal dilating means 29 against the center of the pylorus 150 and progressively dilates the pylorus 150 without tearing or trauma so that the member 20 can be inserted through the pyloric sphincter 155 into the anterior duodenum 160. The surgeon then maneuvers the pyloroplasty/pylorectomy shield 10 and the stapler cartridge 60 such that an anterior section 156 of the pylorus 150 falls into the gap 12 between the proximal end 22 of the member 20 and the distal end 62 of the stapler cartridge 60 (as can be seen in FIG. 8 and FIG. 9). The posterior section 157 of the pylorus 150 which the surgeon does not wish to excise is protected by the shield member 30 such that it is prevented from falling into the previously-mentioned gap 12. Then the surgeon tightens the knob 85 of the stapler 50 such that the shield 10 translates axially in a proximal direction causing the anterior section 156 of pylorus 150 to be firmly engaged in the gap 12 between the anvil 35 and the distal end 62 of the stapler cartridge 60 effective to produce proper stapling. A conventional invaginator, introduced through a 10 mm trocar, may be used by the surgeon to maintain the anterior section 156 within the gap 12 as the shield 10 is translated to engage the section 156 in the gap 12. Then the surgeon actuates the actuating lever 90 which in turn causes the staples contained in the cartridge 60 to be forced through the tissue surrounding the pylorus and formed in the anvil 35, while simultaneously the circular blade 68 cuts out the anterior section 156 of the pylorus 150 contained within the gap 12. As can be seen in FIG. 10 and FIG. 11, the lower end of the stomach 140 has been stapled to the upper end of the duodenum 160. The surgeon then removes the excised section 156 of pyloris 150, the stapler 50 and the shield 10 through the 33 mm trocar cannula 100. Punctures in the stomach wall and the abdominal wall caused by the trocars are closed using conventional techniques including suturing, stapling and combinations thereof.

Although this invention has been shown and described with respect to detailed embodiments thereof, it will be understood by those skilled in the art that various changes in form and detail thereof may be made without departing from the spirit and scope of the claimed invention.

What is claimed is:

1. A method of performing a pyloroplasty/pylorectomy, comprising:
    inserting a circular stapler having a pyloroplasty/pylorectomy shield into the pylorus of a mammal; and,
    actuating the stapler so that a section of the pylorus is removed and adjoining tissue is stapled,
    wherein the pyloroplasty/pylorectomy shield comprises:
        a base member having a proximal end and a distal end;
        anvil means mounted to the proximal end of said member;
        attachment means mounted to said proximal end of said member for engagement with a circular stapler;
    a pyloroplasty/pylorectomy shield member extending axially from the proximal end of said member; and,
    dilation means extending from the distal end of said member.

* * * * *